US006977729B2

(12) United States Patent
Marquardt et al.

(10) Patent No.: US 6,977,729 B2
(45) Date of Patent: Dec. 20, 2005

(54) OPTICAL IMMERSION PROBE INCORPORATING A SPHERICAL LENS

(75) Inventors: Brian J. Marquardt, Bothell, WA (US); Lloyd W. Burgess, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/786,275

(22) Filed: Feb. 24, 2004

(65) Prior Publication Data

US 2004/0165183 A1 Aug. 26, 2004

Related U.S. Application Data

(63) Continuation of application No. 10/055,625, filed on Jan. 23, 2002, now Pat. No. 6,831,745.
(60) Provisional application No. 60/263,442, filed on Jan. 23, 2001.

(51) Int. Cl.[7] ............................................ G01N 21/00
(52) U.S. Cl. ....................................................... 356/436
(58) Field of Search .... 356/432, 436–442; 385/70–72, 385/60, 78, 53, 55, 115–123; 606/2–4, 7, 606/8; 250/341, 343, 573, 574

(56) References Cited

U.S. PATENT DOCUMENTS

| | | | | |
|---|---|---|---|---|
| 5,051,551 A | * | 9/1991 | Doyle | 250/341.2 |
| 5,579,423 A | | 11/1996 | Tanaka et al. | 385/35 |
| 5,688,261 A | | 11/1997 | Amirkhanian et al. | 606/17 |
| 5,693,043 A | | 12/1997 | Kittrell et al. | 606/15 |
| 6,252,661 B1 | | 6/2001 | Hanna | 356/497 |
| 6,416,234 B1 | * | 7/2002 | Wach et al. | 385/70 |
| 6,466,323 B1 | | 10/2002 | Anderson et al. | 356/445 |

OTHER PUBLICATIONS

Alfred, C.D. et al., "Near-infrared Raman Spectroscopy of Liquids and Solids with a Fiber-Optic Sampler, Diode Laser, and CCD Detector," (1990) *Applied Spectroscopy* 44(7): 1229-1231.

Angel, S.M. et al., "Some New Uses for Filtered Fiber-Optic Raman Probes: in Situ Drug identification and in Situ and Remote Raman Imaging," (1999) *J. Raman Spectrosc.* 30: 795-805.

(Continued)

*Primary Examiner*—Michael P. Stafira
(74) *Attorney, Agent, or Firm*—Greenlee, Winner & Sullivan, PC

(57) ABSTRACT

This invention provides a spherical lens optical immersion probe for use in analysis of solids, liquids, gases, powders, suspensions, slurries, particles and other homogeneous or heterogeneous samples. The use of a spherical lens in an optical immersion probe confers many advantages over traditional immersion probes including ease of use and accuracy of focus. The probe of this invention has applications to many types of optical spectroscopy methods including ultraviolet/visible (UV-Vis), near-infrared (NIR), mid-infrared (FTIR), fluorescence, and Raman spectroscopy. The spherical lens used in this invention is both the optical and sample interface in the analytical system, and may be used to both focus the excitation source and to collecting signal. Importantly, this invention has broad applications to any optical analytical technology that necessitates an optical immersion probe.

25 Claims, 11 Drawing Sheets

OTHER PUBLICATIONS

Aust, J.F. et al., "In Situ Analysis of a High-termperature Cure Reaction in Real Time Using Modulated Fiber-optic Ft-raman Spectroscopy," (1999) *Applied Spectroscopy* 53(6):682-686.

Cooney, T.F. et al., "Comparative Study of Some Fiber-optic Remote Raman Probe Designs, Part I: Model for Liquids and Transparent Solids," (1996) *Applied Spectroscopy* 50(7):836-848.

Cooney, T.F. et al., "Comparative Study of Some Fiber-Optic Remote Raman Probe Designs. Part II: Tests of Single-Fiber, Lensed, and Flat- and Bevel-Tip Multi-Fiber Probes," (1996) *Applied Spectroscopy* 50(7):849-860.

Cooney, T.F. et al., "Rare-Earth-Doped Glass Fiber for Background Rejection in Remote Fiber-Optic Raman Probes: Theory and Analysis of Holmium-Bearing Glass," (1993) *Applied Spectroscopy* 47(10):1683-1692.

Dai, S. et al., "Accurate Procedure for Determing the Calibration Curve of High-Temperature Molten Salt Systems via Raman Spectroscopy," (1993) *Applied Spectroscopy* 47(8):1286-1288.

Dai, S. et al., "Temperature Measurement by Observation of the Raman Spectrum of Diamond," (1992) *Applied Spectroscopy* 44:1229-1231.

Gilmore, D.A. et al., "Quantitative Detection of Environmentally Important Dyes Using Diode Laser/fiber-optic Raman Spectroscopy," (1995) *Applied Spectroscopy* 49(4):508-511.

Lin, L-T et al., "Feasibility of Quantitative Uv Resonance Raman Spectroscopy with a Krf Excimer Laser," (1987) *Applied Spectroscopy* 41:422-427.

Ma, J. et al., "Fiber Raman Background Study and its Application in Setting up Optical Fiber Raman Probes," (1996) *Applied Optics* 35(15):2527-2533.

Marquardt, B.J. et al., "Demonstration of a High Precision Optical Probe for Effective Sampling of Solids by Raman Spectroscopy," (Oct. 2001) *Proc. SPIE* vol. 4469:62-69, Raman Spectroscopy and Light Scattering Technologies in Materials Science, David L. Andrews; Ed.

McCreery, R.L. et al., "Fiber Optic Probe for Remote Raman Spectrometry," (1983) *Anal. Chem.* 55:146-148.

Schwab, S.D. et al., "Remote, Long-Pathlength Cell for High-Sensitivity Raman Spectroscopy," (1987) *Applied Spectroscopy* 41:126-130.

Schwab, S. D. et al., "Normal and Resonance Raman Spectroelectro-Chemistry with Fiber Optic Light Collection," (1986) *Anal. Chem.* 58:2486-2492.

Trott, G.R. et al., "Angualr Resolved Raman Scattering Using Fiber Optic Probes," (Nov. 1980) *Reb. Sci. Instrum.* 51(11):1493-1496.

Wang, C. et al., "In Situ Monitoring of Emulsion Polymerization Using Fiber-Optic Raman Spectroscopy," (1992) *Applied Spectroscopy* 46(11):1729-1731.

Xiao, H. et al., "Quantitative Raman Spectral Measurements Using a Diamond-Coated All-Silica Fiber-Optic Probe," (1998) *Applied Spectroscopy* 52:626-628.

Zheng, X. et al., "Self-Referencing Raman Probes for Quantitative Analysis," (2001) *Applied Spectroscopy* 55(4): 382-388.

* cited by examiner

OPTICAL IMMERSION PROBE INCORPORATING A SPHERICAL LENS

CROSS-REFERENCE TO RELATED APPLICATIONS

This application is a continuation of U.S. patent application Ser. No. 10/055,625, filed Jan. 23, 2002, now U.S. Pat. No. 6,831,745, and claims the benefit of the filing date of U.S. Provisional Application Ser. No. 60/263,442 filed Jan. 23, 2001 entitled "Optical Immersion Probe Incorporating a Spherical Lens" both of which are incorporated herein to the extent not inconsistent herewith.

BACKGROUND OF THE INVENTION

On-line and in-line analytical measurements are routinely performed for environmental and industrial process monitoring and control. Many of the specific measurements made in these fields are performed using spectroscopic probes, which are inserted into the sample to be analyzed. These types of probes are generally referred to as 'immersion probes.' These probes are found in many shapes, sizes and optical configurations specific to a certain process or sample being analyzed. The need for the multitude of different optical probe designs stems from the varying samples they are designed to measure. These samples range from pure liquids, pastes, slurries, powders, solids and gases at varying temperatures, pressures and pH's.

Many immersion probe designs are intricately engineered with numerous moving parts and optical components. The addition of moving parts to allow an operator to align/focus a probe leads to imprecision during repeated analyses. The measurement errors may be due to misalignment, focus/alignment drifting over time or numerous operators having different optimization criteria. The addition of multiple optical interfaces can also lead to measurement imprecision when using immersion probes. Flat faced optical probes have a tendency to collect material on the optic in contact with the sample, thereby degrading performance over time. Many probes use a focusing (movable) optic in the barrel of the probe that is focused through a flat window that is in contact with the sample. Most immersion probes operate with a focusing lens that illuminates a portion of the sample that is some fixed distance from the physical tip of the probe (either window or lens). This common probe design leads to imprecision due to changing focal length and tip fouling and increases light scattering due to particles in a sample, changes in optical density and other physical variations in sample properties.

There is a need in the art for a single robust, straightforward, versatile and precise optical probe for use with various spectroscopic techniques to analyze all types of samples. The fact that the focal volume of the probe is a constant at the surface of the optical element in contact with the sample ensures accurate optical focus with whatever type of sample is present.

This invention provides a number of attributes not available in known optical immersion probes: 1) precise focus on any surface or material; 2) no need for sample alignment; 3) ease of sampling—simply place probe into or onto sample; 4) ability to be used in flowing/static sampling systems; 5) analysis not affected by directional flows or variable contact points; 6) analysis not affected by differential light scattering or particle distribution of solid particles; and 7) fully sealed probe element is highly durable in harsh process/analytical environments. Thus, this invention circumvents the need for a multitude of imprecise complicated optical probes to measure samples ranging from gases to liquids to solids.

SUMMARY OF THE INVENTION

A novel optical probe is provided utilizing a spherical lens as both the optical and sample interface for applications including laboratory and process analysis applications. The spherical lens optical immersion probe (also called a ball probe) is an efficient sampling interface for the analysis of many types of samples including solids, powders, slurries, suspensions, particles, vapors, liquids and the like. The samples may be homogeneous, heterogeneous, or comprised of multiple phases. The probe design is compact, durable and straightforward with no moving or easily fouled components. The spherical lens probe has been demonstrated to greatly improve the precision of spectroscopic measurements (e.g. ultraviolet/visible (UV-Vis), near-infrared (NIR), mid-infrared (FTIR), fluorescence, and Raman) of a variety of samples over other known optical immersion probes. Importantly, this invention has broad applications to any optical analytical technology that necessitates an optical immersion probe.

The precision of the optical immersion probe of this invention is due to its novel design whereby a spherical lens is used as both the light focusing element and the optical interface with the sample. As such, the probe may also serve as a light collecting lens or device for optical signal collection. For example, in Raman spectroscopy, scattered light is collected by the spherical lens and directed to the instrumentation for analysis. This optical design provides a constant and precisely positioned focal volume, located directly on the proximal face of the spherical optic, for the excitation source of the various optical analyses, which leads to greatly increased measurement precision.

Further precision enhancement is gained by choosing a spherical lens having a focal point close to the surface of the spherical lens. Typically, the focal point is from about 50 $\mu$m to about 200 $\mu$m from the apex of the spherical lens. This ensures that any sample in contact with the spherical lens is properly focused to perform an optimal optical measurement. This design element eliminates the measurement imprecision due to path length variations inherent in other optical immersion probe designs.

FIG. 1 shows the theoretical optical path of a collimated optical beam through the spherical lens. For example, a focal length of about 200 $\mu$m from the apex of the spherical lens surface has been determined when a collimated 3 mm diameter 785 nm laser beam illuminates the surface of the spherical lens opposite the surface in contact with the sample. There is also no need for optical focusing of this probe onto/into the sample because the sample is optimally focused when it is in contact with the spherical lens. This makes the spherical lens optical immersion probe of this invention a focus free immersion probe with the only sampling condition being that the spherical lens itself must be in contact with the sample.

In its simplest embodiment, the immersion probe of this invention comprises a spherical lens attached to one end of a cylinder (the probe tip) in such a way that the end of the cylinder immersed in the sample (herein the 'proximal end') is substantially sealed and leak-proof. The seal can be provided by welding or braising the lens to the probe tip, or by using epoxy or other adhesives to fix the lens to the cylinder. Preferably the seal is provided by braising a sapphire lens to a metal or alloy cylinder. In other preferred embodiments, the lens is secured at the proximal end of the probe tip by using a combination of gaskets or o-rings and additional threaded tubes to provide force to the gaskets sufficient for a leak-proof seal.

As used herein, the term 'gasket' is used to refer to a pressure-tight seal made of any deformable material such as polymers, rubber, plastic, metals such as copper and gold, etc . . . Gaskets can be any shape, including the specific round shape of an o-ring.

Throughout the specification the term "leak proof seal" or substantially leak proof is used to describe a seal sufficient to close the interfaces in the optical immersion probe so as to prevent material from entering (or leaving) the interior of the optical immersion probe. The seal must be sufficient to prevent corruption of the analytical results. The quality of the seal is a measure of how much pressure the seal can withstand without leaking and is dictated in part by choice of sealing material (epoxy, weld, o-ring composition, etc. Those skilled in the art are readily able to recognize how to choose and apply materials that will provide sufficient seals for a given application. For example, the immersion probe described in this disclosure was constructed using 316 stainless steel tubing, Chemraz® 505 o-rings (Green Tweed, Inc.), and a synthetic sapphire spherical lens. The use of Chemraz® 505 o-rings has been shown to provide an optical immersion probe that is leak-proof to greater than 600 psi Helium. Alternative embodiments using sapphire braising resulted in an immersion probe that is leak proof to greater than 1000 psi Helium.

Embodiments described below use tubing that is circular in cross-section, but tubing having any geometric shape in cross-section may be adapted for use in the invention.

In preferred embodiments, tubes are comprised of metals or metal alloys. Preferred materials include stainless steel and Hastelloy®. However, any material may be used, including plastics, ceramics, ceramic composites, glass, or other materials known in the art. Tubes may be either rigid or flexible. In probes where the excitation source is provided as a collimated beam, the tube material should be sufficiently rigid so that optical alignment of the excitation source with the lens is maintained. Flexible tube materials may be used when the excitation source is directly coupled to the spherical lens, as in the case of a fiber optic cable positioned within the tube, for example.

Gaskets or o-rings are typically rubber, but may also be any elastomeric material or metal capable of conforming to the spherical lens so as to provide a sufficient seal for the application. Factors to consider in the choice of o-rings include chemical compatibility, compressibility, temperature resistance, structural strength, etc. as dictated by the application environment and as known to one of ordinary skill in the art.

Preferably, tubing and gasket materials are selected from materials that are substantially chemically resistant to the chemical environment in which the probe is used. That is, the materials resist corrosion that could lead to failure of the structure (such as the seal) or interference with the measurement. Such materials are known in the art, and one skilled in the art would be able to select materials appropriate for different chemical environments. Tubing and gaskets are also chosen to withstand temperatures and pressures encountered during the analysis.

In preferred embodiments, a sapphire spherical lens was used because of sapphire's resistance to scratching and transparency over a wide range of wavelengths. The sapphire lens may be synthetic. However, any lens material known in the art may be used including, but not limited to fused silica, glass, doped glass, ruby, diamond, cubic zirconia, zinc selenide, potassium bromide crystal and sodium chloride crystal. Impurities and/or crystalline defects may or may not be present in the lens materials. Similarly, the size of the spherical lens can be readily chosen by one skilled in the art when considering the wavelength of light, optical geometric compatibility and the desired focal length/volume. Furthermore, the term 'spherical' as used herein refers to any rounded object approximating the form of a geometric sphere as long as the optical properties of that object are sufficient to carry out the invention as described.

The immersion probe utilizing a sapphire spherical lens has been demonstrated for the analysis of various solids, powders, slurries, suspensions, particles, vapors and liquids with very good analytical performance.

DETAILED DESCRIPTION OF THE INVENTION

As used herein, the term 'proximal' refers to the end of the device or any of the device components that is nearer to the interface with a sample. The term 'distal' refers to the end of the device or any of the device components that is opposite the proximal end, and nearer the instrument interface.

Figure 1:
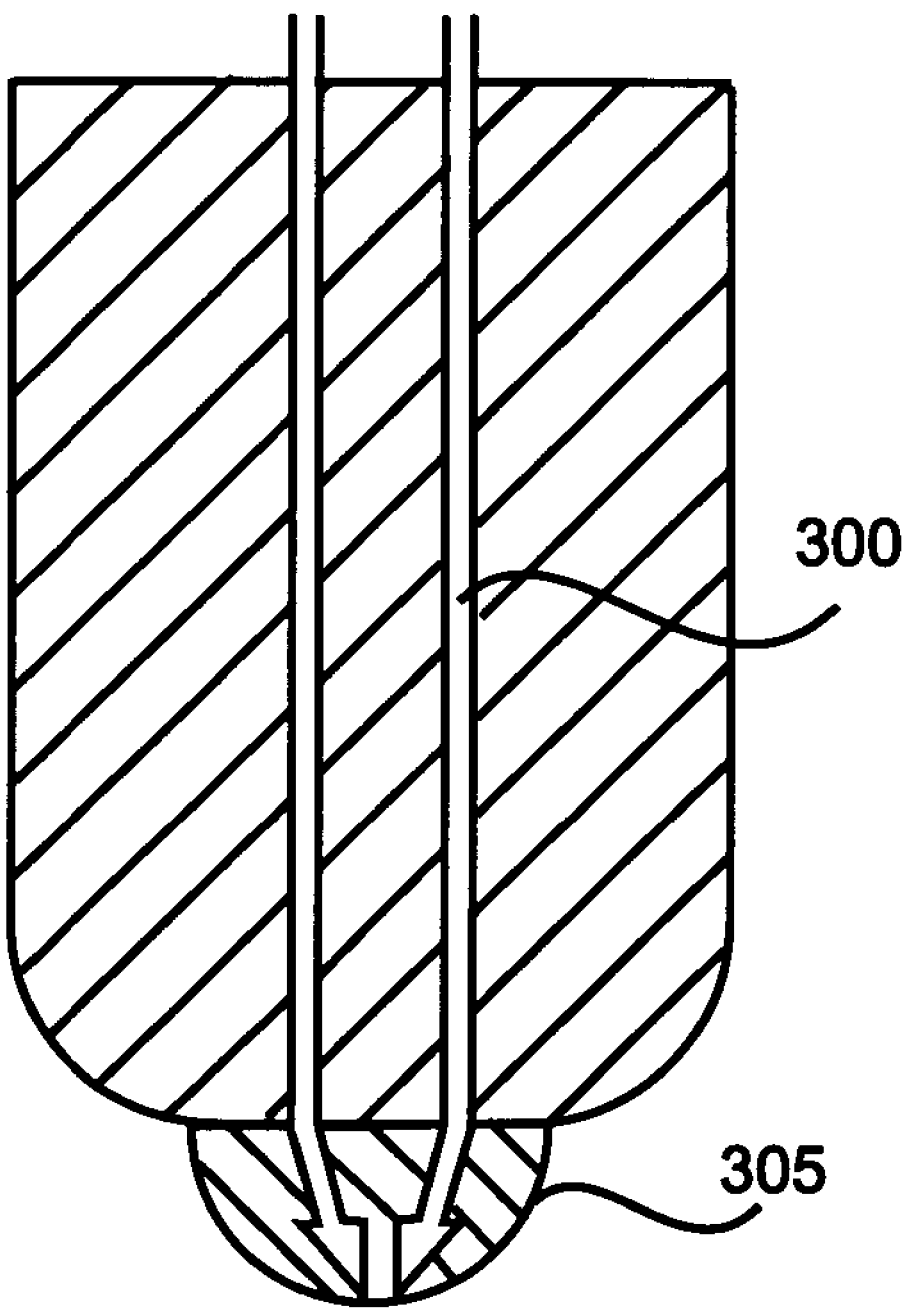
FIG. 1: Optical pathlength of light focused at the end of the spherical lens optical immersion probe.
Figure 2:
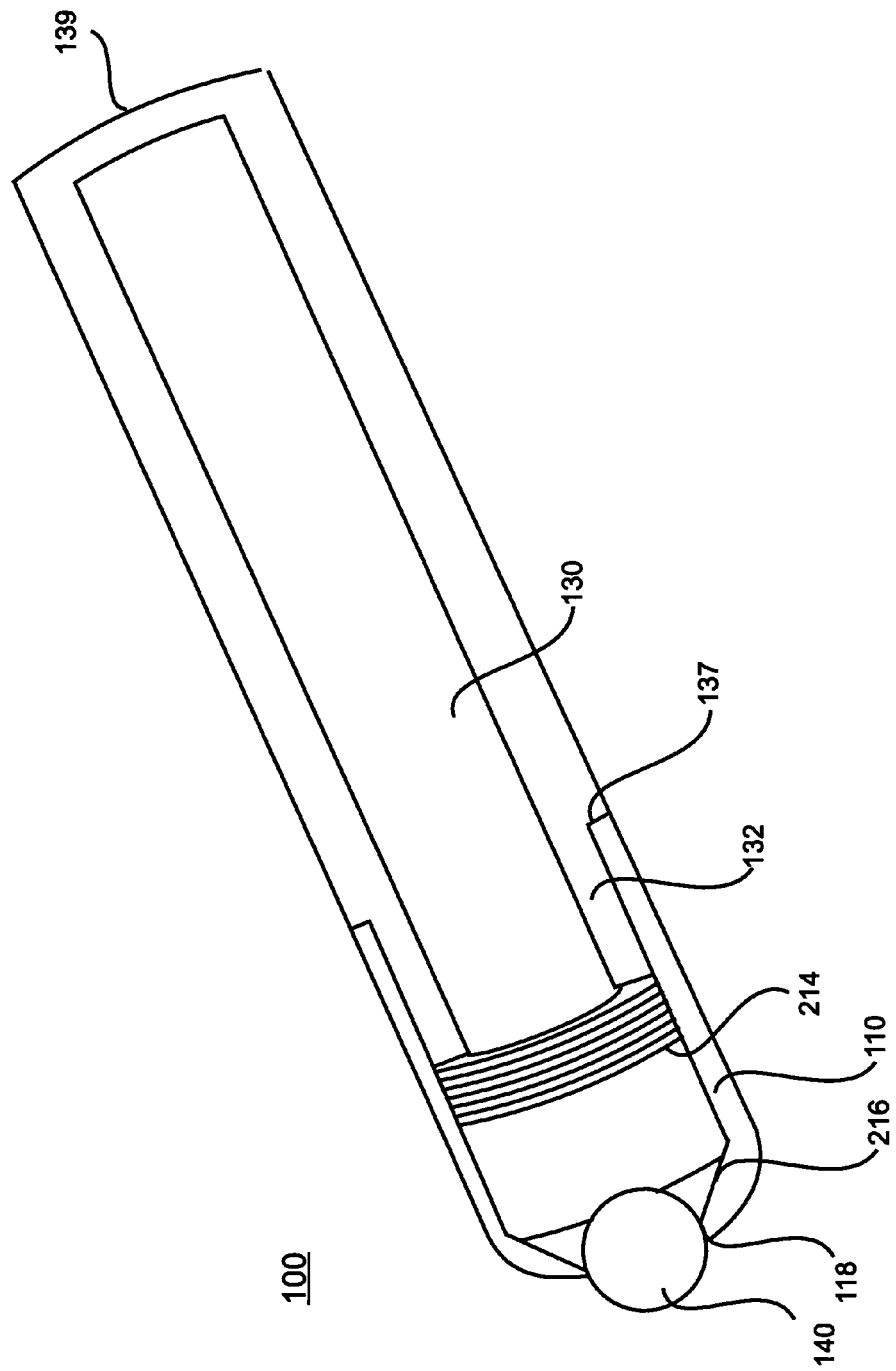
FIG. 2: One embodiment of the spherical lens optical immersion probe.

The simplest embodiment of the immersion probe of this invention is illustrated in FIG. 2. In this embodiment, probe 100 comprises spherical lens 140 seated within cylindrical probe tip 110 at lens opening 118. A seal between the probe tip and the lens is formed at the opening by any means known in the art, including all forms of welding or braising and the use of epoxies or other adhesives. Probe tip 110 may be any length. Optionally, probe tip 110 may have threads 214 on its interior surface and may be extended using probe tube 130, which has threaded collar 132 for threading into probe tip 110. A seal is optionally formed between probe tube lip 137 and the distal end of probe tip 110.

Figure 3A:
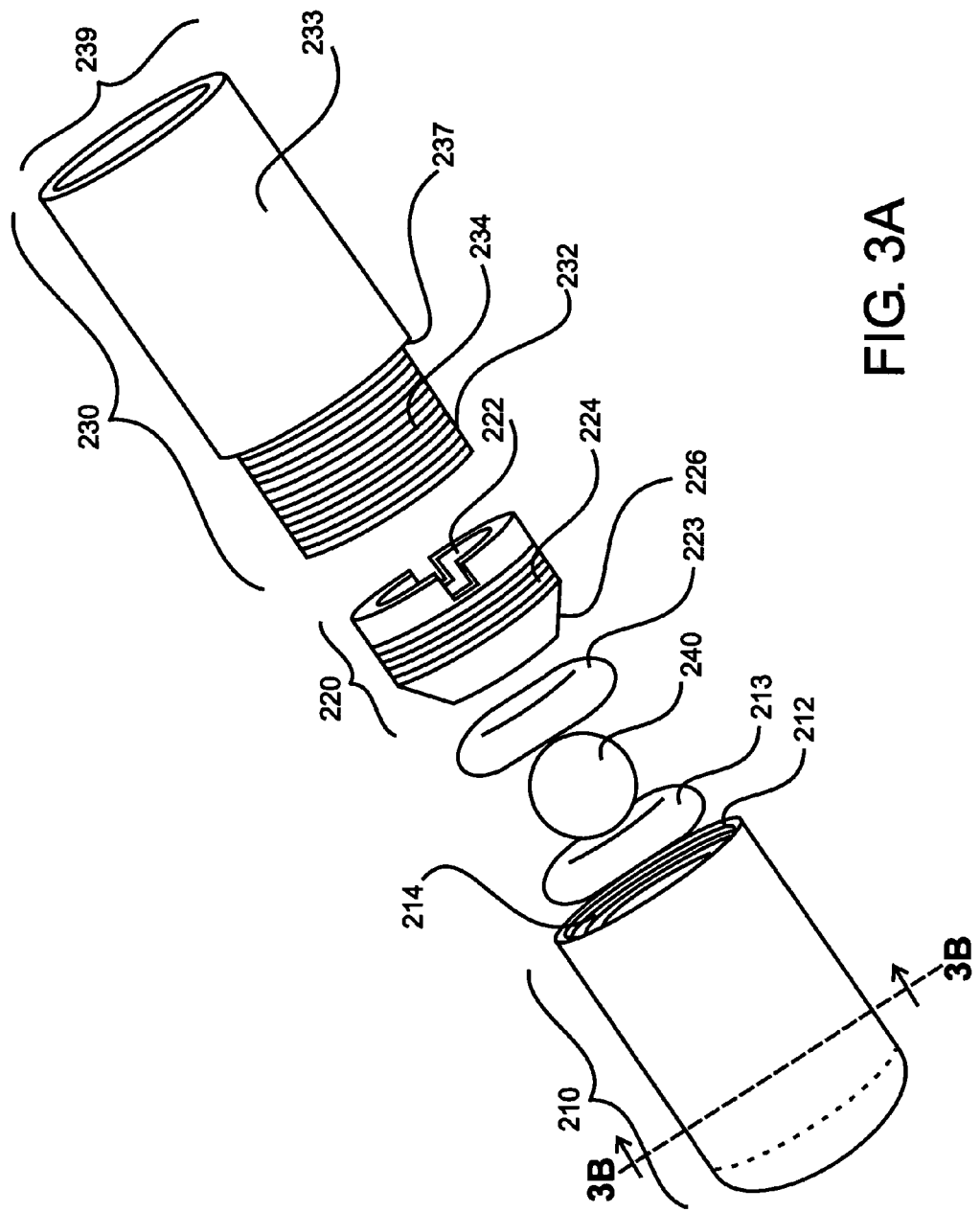
FIG. 3: Two views of a preferred embodiment of the spherical lens optical immersion probe. 3A) an exploded view; 3B) a cross section of 3A through 3B—3B.
Figure 3B:
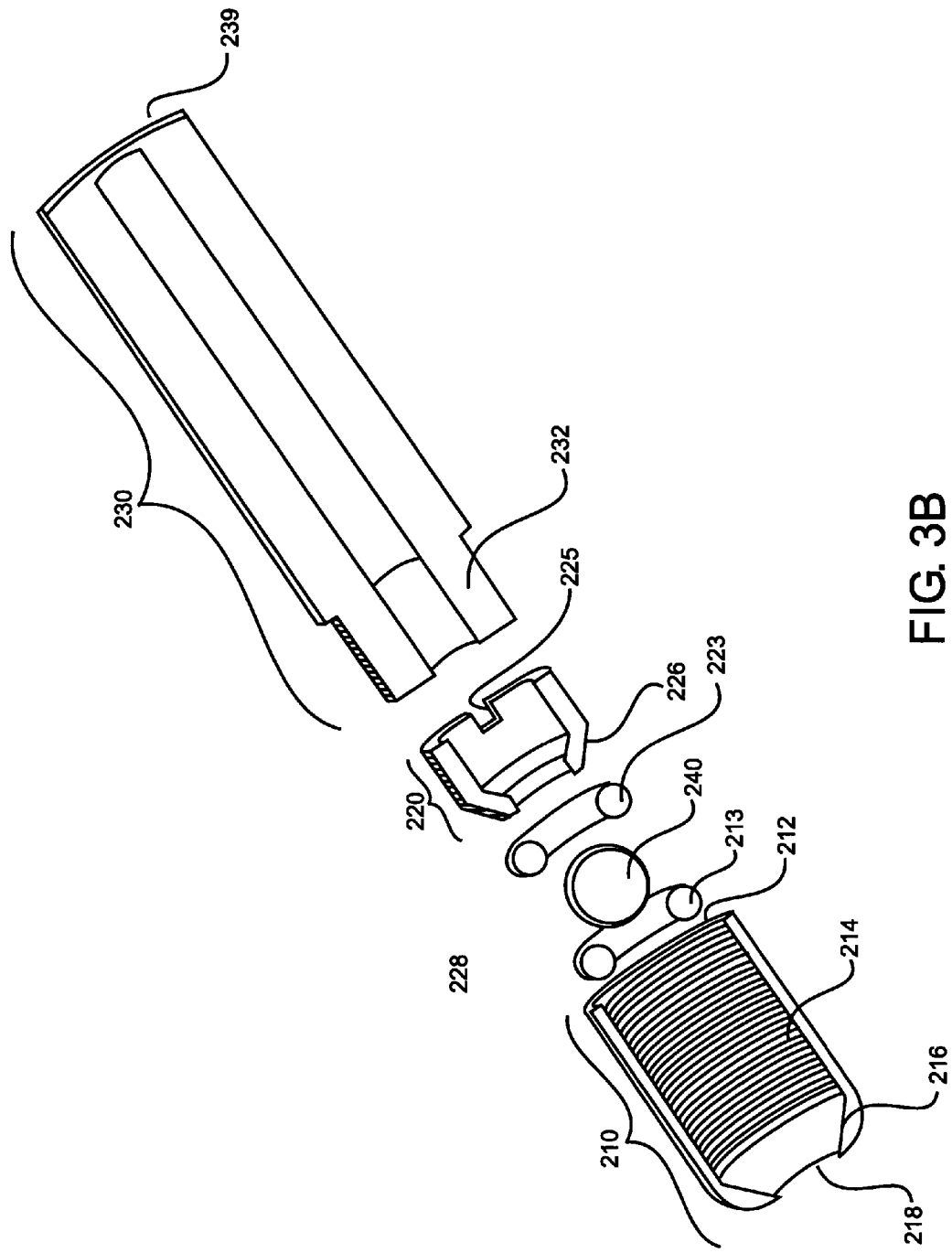

FIG. 3 illustrates a preferred embodiment of the optical immersion probe of this invention. Probe 200 comprises 4 components: spherical lens 240, probe tip 210, fastener 220 and probe tube 230. Additional elements such as gaskets, o-rings, and other sealing means may be present to provide a leak proof system. In this embodiment, o-ring 213 is placed inside probe tip 210 such that it is seated around lens opening 218 on chamfered edge 216 at the proximal end of probe tip 210. Lens 240 is also placed inside probe tip 210 such that it is seated on top of o-ring 213 and a portion of the lens extends through lens opening 218 and is external to probe tip 210. Lens 240 is held in place, and a seal between the lens and the probe tip is formed, by fastener 220. O-ring 223 is seated in probe tip 210 on top of lens 240. Fastener 220 has fastener threads 224 on its exterior surface and has chamfered edge 226, around which o-ring 223 is seated when fastener 220 is inserted into probe tip 210. Threads 224 on fastener 220 are mated with tip threads 214 on the interior surface of probe tip 210. Fastener 220 is threaded into probe tip 210 such that o-ring 223 is seated between lens 240 and chamfered edge 226 of fastener 220. This applies pressure on lens 240 such that a seal is formed at lens opening 218. Notch 225 is provided so that a screwdriver or other such device can be used to turn fastener 220 and provide greater force to the interfaces between the probe tip, o-rings, and spherical lens. The amount of force applied is a function of the type of o-ring material used as well as the experimental conditions, including pressure. This force would be readily determined by one skilled in the art. Furthermore, the chamfered edges as illustrated in FIGS. 2 and 3 are examples only. The pitch of the chamfered edges may be steeper or shallower, or the edge may be beveled, slanted, rounded, square.

Probe tube 230 is connected to the probe tip by mating threads 234 on threaded sleeve 232 with tip threads 214 located on the interior surface of probe tip 220. This mating may provide additional force to the seal system. The interface between probe tip 210 and probe tube 230 may be welded or otherwise sealed using epoxies or other adhesives. Alternatively, an additional o-ring (not shown) may be provided between probe tube lip 237 and probe tip 210.

In another embodiment, fastener 220 may be made as one piece with probe tube 230 at the proximal end of threaded sleeve 232.

The opening at the distal end of probe tube 230 is provided as an instrument interface (239). Instrument interface 239 is coupled to an analytical instrument using any means known in the art including threads, mechanical couplers such as Swage connectors, quick connectors, and other connectors. These and other interface mechanisms would be readily known to one skilled in the art.

EXAMPLES

The following examples illustrate the use of the optical immersion probe of this invention for Raman spectroscopy. These examples are not meant to limit the use of the spherical lens optical immersion probe to Raman spectroscopy and those skilled in the art will recognize the utility of the probe of this invention to other spectroscopic and optical measuring techniques.

In the following section, the use of the spherical lens optical immersion probe of this invention for performing high precision Raman measurements of various solid sample systems is discussed. The optical and mechanical design of the probe has been described above. In one example, the analytical performance of the probe is demonstrated by comparing the data from the spherical lens probe to that of a commercially available immersion probe. The commercially available probe had a flat faced window in contact with the sample. An adjustable plano-convex focusing optic was behind the window and adjustable with respect to the window surface so as to change the depth of focus into the sample to be analyzed.

Experimental

Raman spectra were collected with a Kaiser Optical Systems Hololab Series 5000 Raman instrument consisting of a Holoprobe transmission holographic spectrograph interfaced with fiber-optics to a Mark II™ holographic probe head. The fiber-optic probe head was equipped with a custom-built immersion probe incorporating a spherical sapphire lens. The Raman system was equipped with a 785 nm stabilized external cavity diode laser (SDL Inc.) operating at an average power of 90 mW at the sample. The Mark II™ holographic probe head was coupled to the laser with an 8 $\mu$m i.d. single mode excitation fiber and the scattered signal was collected using a 50 $\mu$m i.d. multimode fiber. The immersion probe was 10.5 inches long and the spherical sapphire lens was used to both focus the laser and collect the scattered radiation in an epi-illumination configuration. All Raman spectra were collected using a 50 $\mu$m slit width and a detector temperature of –40° C. All spectra were acquired while vigorously stirring the sample volume unless stated otherwise.

Example 1

Analysis of Acrylic Paint

In this experiment, Raman spectroscopy was performed in a sample of white acrylic paint to compare the performance of the spherical lens optical immersion probe of this invention to a commercially available Raman immersion probe, using the same Raman instrument described above.

Figure 4:
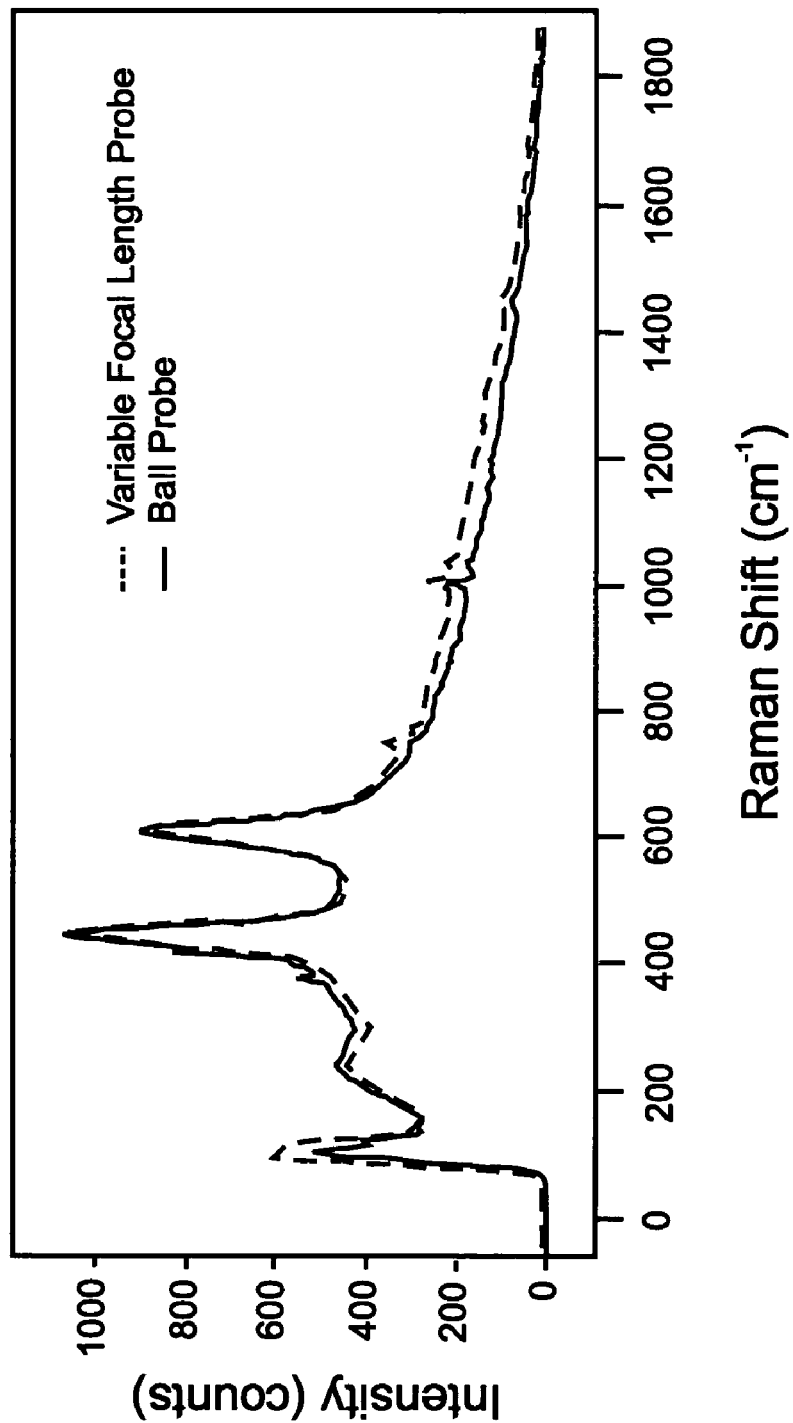
FIG. 4: White acrylic paint analysis using both a variable focal length immersion probe and the spherical lensed probe.

The data from the experiment are shown in FIG. 4. The Raman peaks of the whitening agent, $TiO_2$, were used for comparison in the experiment. The initial results from this experiment were very promising. The spherical lensed immersion probe was placed into the paint sample five separate times with no alignment or adjustment of its position/focus. A spectrum (5 sec. exposure, 10 accumulations) was collected after the probe was submerged in the white acrylic paint sample. The same was done with the commercial probe, after it was aligned for optimal focus before the first measurement.

The relative sensitivity of the two probes was comparable, however the measurement reproducibility of the two probes was significantly different. Over the five measurements performed, the $TiO_2$ peak intensities with the commercial probe had a relative standard deviation (RSD) of 1.84% compared to the spherical lensed immersion probe's 0.24% RSD. The spherical lensed immersion probe performed well in this experiment, especially since no operator input was needed to perform the analysis compared with the commercial probe. The optical design of the spherical lens optical immersion probe worked very well in a high weight percent slurry sample such as paint.

Example 2

Agglomerates of Silica Particles

Figure 5:
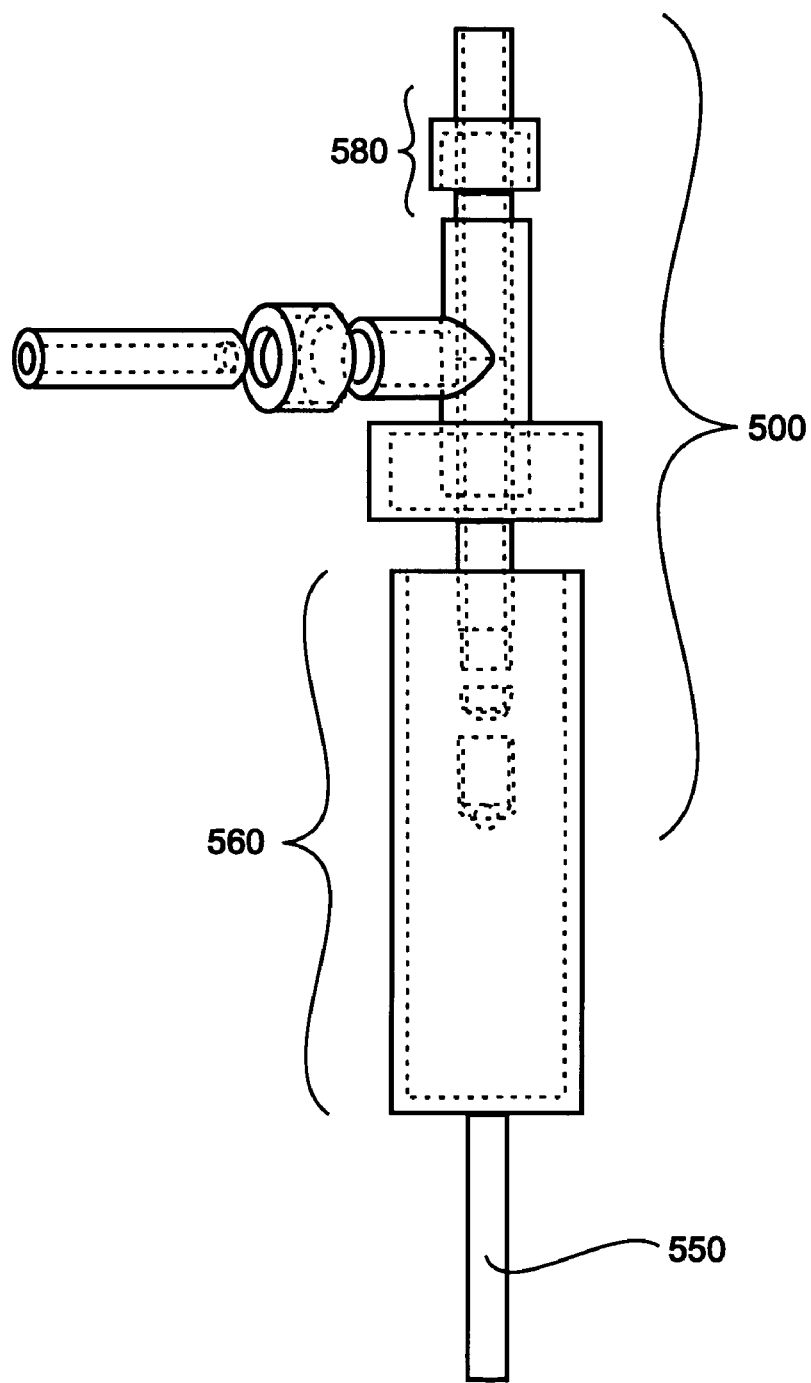
FIG. 5: Experimental setup of fluidized bed incorporating immersion probe.

The sampling apparatus for the mixing experiments described in Examples 2 and 3 below is shown in FIG. 5.

The sampling apparatus consisted of a tubular fluidized bed reactor 560 equipped with a dry nitrogen gas inlet 550 for mixing. The spherical lens optical immersion probe 500 was compression sealed in the reactor from above with a Swagelok pressure fitting 580.

Agglomerates of <1 µm silica particles powder coated with polydimethylsiloxane (PDMS) polymer were analyzed with Raman spectroscopy. The silica particles were placed in the vessel and fluidized (actively mixed) by flowing dry nitrogen through the vessel. The immersion probe was positioned in the fluidized sample to ensure constant contact with the turbulent sample.

Figure 6:
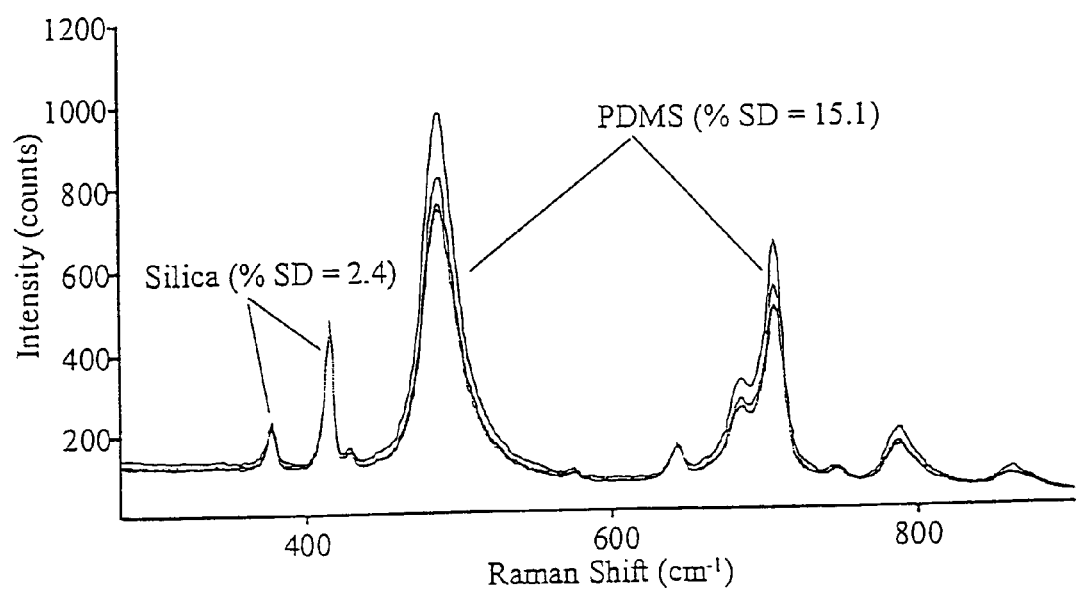
FIG. 6: Silica particles (<1 $\mu$m diameter) coated with PDMS. The 5 spectra were obtained while the particles were fluidized.

The results of five spectra taken over a five minute time period during this experiment are shown in FIG. 6. Each spectrum was the average of five, five-second accumulations. The spectra consisted of Raman peaks corresponding to both the silica substrate and the PDMS polymer coating on the particles. Interestingly, the RSD of the silica band intensities was only 2.4% compared to the PDMS bands that exhibited a RSD of 15.1%. After repeated experiments using this sample it was apparent that the PDMS coating on the silica particles varied greatly when compared to the silica particles themselves. When the fluidized sample data was compared to the data taken of the sample not actively mixing, the RSDs of the silica and PDMS are 0.76 and 0.72% respectively, for five replicate measurements. These consistent results demonstrated that the Raman spherical lens optical immersion probe was a reproducible means for monitoring coating uniformity of these actively mixed particles.

Example 3

Mixing Analysis of Two Powders

The optical immersion probe of this invention was used to monitor the active mixing of different concentrations of citric acid in 25 g of sucrose. These samples were chosen for their relatively similar densities, particle sizes and ease of disposal.

Figure 7A:
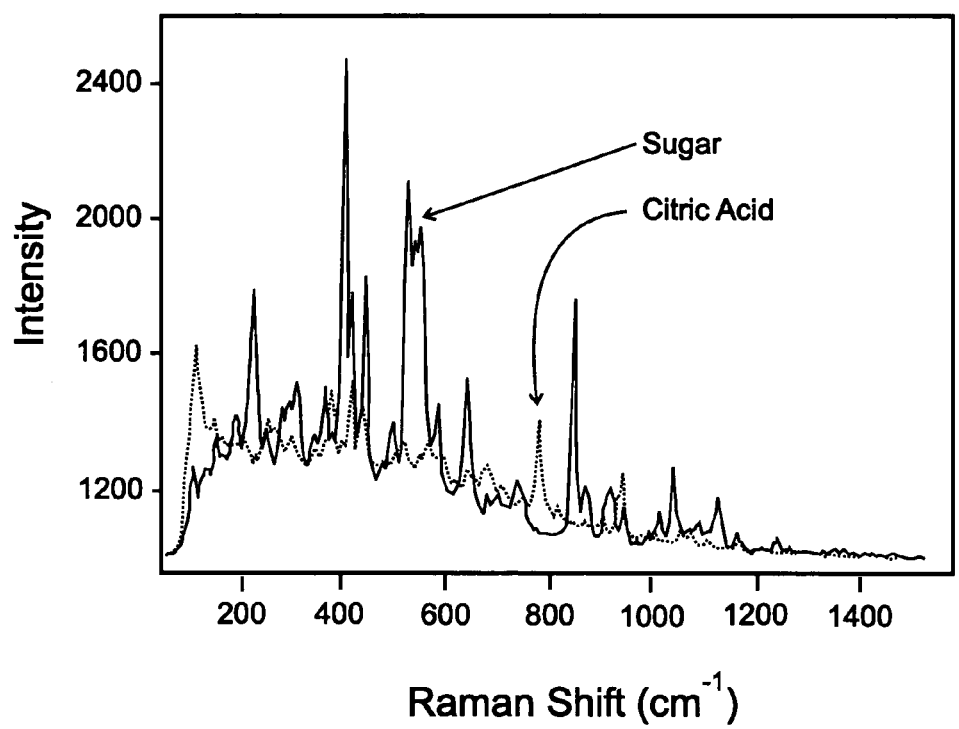
FIG. 7: Powder mixing analysis with Raman immersion probe. 7A) standard Raman spectra of sucrose and citric acid (CA); 7B) PLS calibration of CA for concentrations of 1, 5, 10, 20, 25 and 30% in 25 g of sucrose (60 spectra per concentration); 7C) factor 1 scores of PLS model, sample number correspond to concentration CA-1%=1–60, 5%=61–120, . . . 30%= 300–360.
Figure 7B:
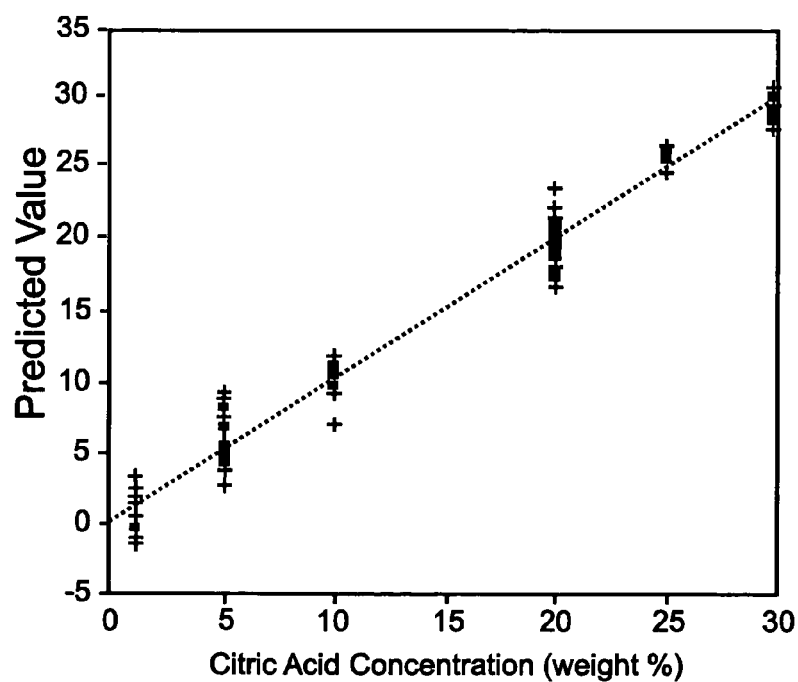
Figure 7C:
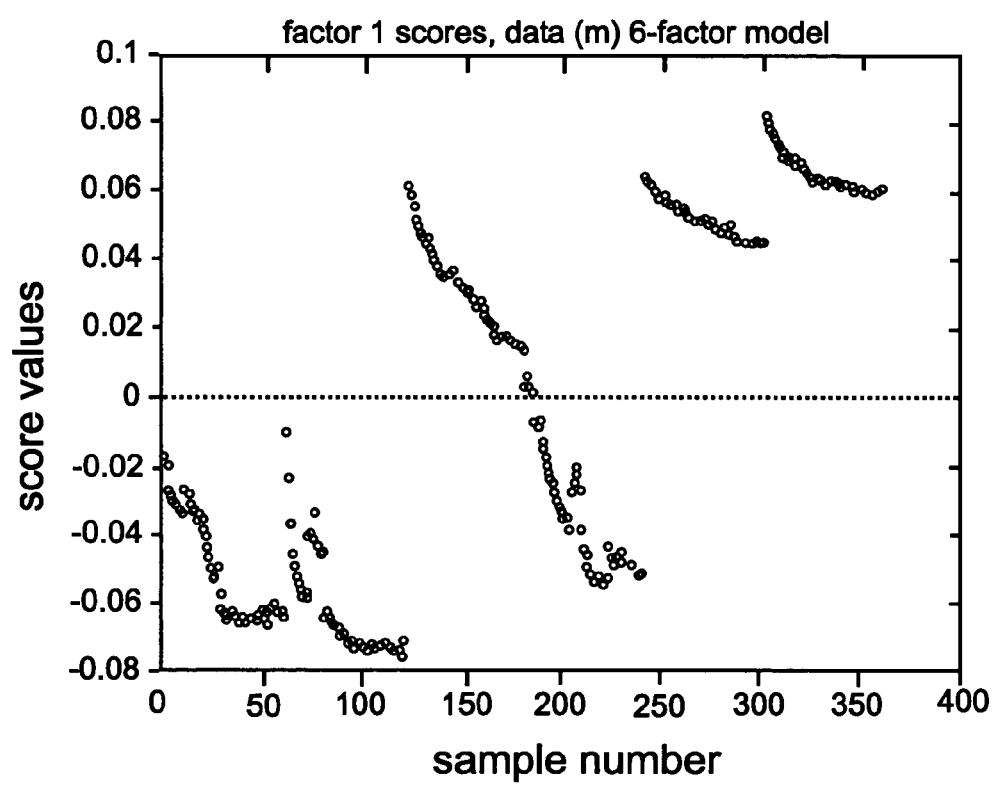

The standard Raman spectra for both citric acid and sucrose are demonstrated in FIG. 7A. The two Raman spectra are quite similar except for the citric acid peak that occurs near 800 cm$^{-1}$. Each spectrum was the average of five, five-second accumulations. The mixing experiment entailed placing both powdered samples into the fluidized bed, creating a 2-layer system. The data collection was then started followed by the start of the gas flow to begin the mixing process.

A total of 60 Raman spectra were obtained for each concentration of citric acid (1–30%). The citric acid concentration range was 1–30% (w/w) in 25 g of sucrose. The performance of the Raman immersion probe for measuring citric acid in a citric acid/sucrose mixture is illustrated in FIG. 6B. The calibration results from the PLS analysis were $r^2=0.987$, RMSC=1.2% and correlation of 0.993. The distribution of data points for each citric acid concentration is representative of the mixing of the citric acid into the sucrose. The fluidization of the 2 layers of powder was correlated with the onset of data collection. The mixing information is described primarily in the first scores plot of the 6 factor model as shown in FIG. 6C. From the loadings data for this factor it was determined that the data are describing the dilution of the initial concentration of sucrose as the two powders are blended. This is most apparent in FIG. 6C for the first two citric acid concentrations (samples 1–60, 61–120) where the scores plots level off indicating nearly complete mixing of the sample. This leveling off of the data is not as apparent at the higher concentrations. It is believed that this is primarily an experimental effect due to limited gas flow through the bed to completely fluidize the higher masses of powder. Recent experiments have also shown that due to the limited volume of the fluidized bed that the higher mass samples should have been fluidized for longer periods of time to achieve complete mixing. Therefore the data shown for the higher masses of citric acid in FIG. 6C had not achieved complete mixing when the experiment was stopped. Because of the sample-to-sample reproducibility of the immersion probe of this invention, specific models and algorithms may be developed for describing and predicting the degree of mixing achieved in various mixers and blenders.

Example 4

Real-Time Reaction Monitoring of Polymorph Formation

Figure 8B:
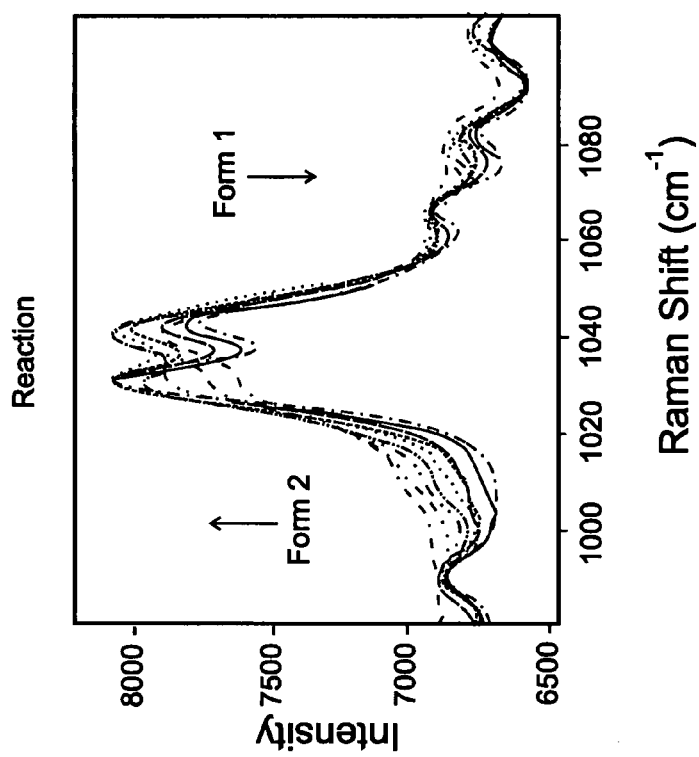
FIG. 8: Raman analysis of real-time polymorph formation. 8A) Raman spectra of pharmaceutical standards; 8B) Series of Raman spectra over 24 hours of mixing the two forms at 40° C.
Figure 8A:
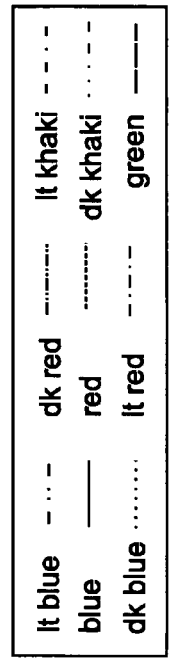
Figure 8A:
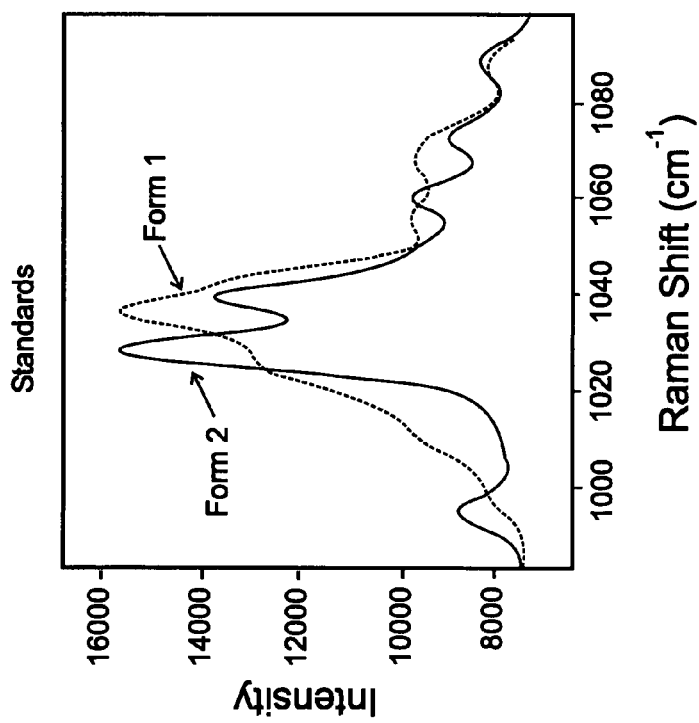
Figure 9:
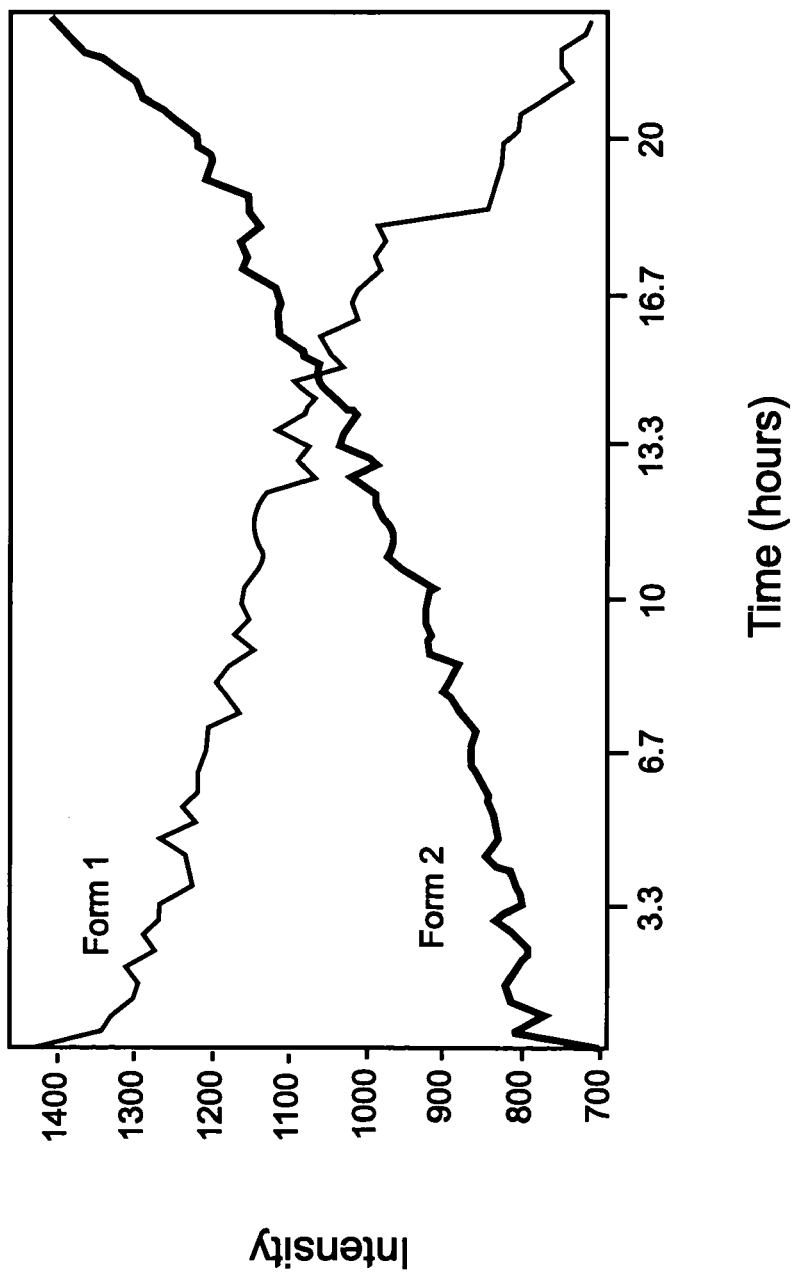
FIG. 9: Analysis of Raman intensity attributed to each form vs. time.

Two crystalline forms of a commercially available active pharmaceutical compound were vigorously stirred in a slurry over 24 hours at 40° C. The transformation of Form 1 into Form 2 was followed by Raman Spectroscopy. Raman spectra of isolated forms of Form 1 and Form 2 are shown in FIG. 8A. FIG. 8B shows a series of Raman spectra taken over 24 hours of vigorous mixing. This series shows the transformation of Form 1 into Form 2. FIG. 9 is an analysis of peak intensity.

All references cited herein are incorporated by reference in their entirety to the extent not inconsistent with the disclosure herein.

Preferred embodiments described above are intended to be illustrative of the spirit of this invention. Numerous variations and applications will be readily apparent to those skilled in the art. The range and scope of this patent is defined by the following claims and their equivalents.

REFERENCES

1. G. R. Trott and T. E. Furtak, "Angular resolved Raman scattering using fiber optic probes", *Rev. Sci. Instrum*, 51, 1493–1496, November 1980.
2. R. L. McCreery, M. Fleischmann, and P. Hendra, "Fiber Optic Probe for Remote Raman Spectrometry", *Anal. Chem*, 55, 146–148, 1983.
3. S. D. Schwab, R. L. McCreery, "Normal and Resonance Raman Spectroelectrochemistry with Fiber Optic Light Collection", *Anal. Chem*, 58, 2486–2492, 1986.
4. S. D. Schwab, R. L. McCreery, "Remote, Long-Path-length Cell for High-Sensitivity Raman Spectroscopy", *Applied Spectroscopy*, 41, 126–130, 1987.
5. L. Lin, C. K. Mann, and T. J. Vickers, "Feasibility of Quantitative UV Resonance Raman Spectroscopy with a KrF Excimer Laser", *Applied Spectroscopy*, 41, 422–427, 1987.
6. C. D. Allred and R. L. McCreery, "Near-Infrared Raman Spectroscopy of Liquids and Solids with a Fiber-Optic Sampler, Diode Laser, and CCD Detector", *Applied Spectroscopy*, 44, 1229–1231, 1990.
7. S. Dai, G. Mamantov, G. M. Begun, J. E. Coffield, and J. P. Young, "Temperature Measurement by Observation of the Raman Spectrum of Diamond", *Applied Spectroscopy*, 46, 375–377, 1992.

8. C. Wang, T. J. Vickers, J. B. Schlenoff, and C. K. Mann, "In Situ Monitoring of Emulsion Polymerization Using Fiber-Optic Raman Spectroscopy", *Applied Spectroscopy*, 46, 1729–1731, 1992.
9. S. Dai, G. Mamantov, G. M. Begun, J. E. Coffield, and J. P. Young, "Accurate Procedure for Determining the Calibration Curve of High-Temperature Molten Salt Systems via Raman Spectroscopy", *Applied Spectroscopy*, 47, 1286–1288, 1993.
10. T. F. Cooney, C. L. Schoen, S. K. Sharma, and D. M. Carey, "Rare-Earth-Doped Glass Fiber-Optic Raman Probes: Theory and Analysis of Holmium-Bearing Glass", *Applied Spectroscopy*, 47, 1683–1692, 1993.
11. D. A. Gilmore, D. Gurka, and M. B. Denton, "Quantitative Detection of Environmentally Important Dyes Using Diode Laser/Fiber-Optic Raman Spectroscopy", *Applied Spectroscopy*, 49, 508–511, 1995.
12. J. Y. Ma, and Y. S. Li, "Fiber Raman background study and its application in setting up optical fiber Raman probes", *Applied Optics*, 35, 2527–2533, 1996.
13. H. Xiao, S. Dai, J. P. Young, C. S. Feigerle, and A. G. Edwards, "Quantitative Raman Spectral Measurement Using a Diamond-Coated All-Silica Fiber-Optic Probe", *Applied Spectroscopy*, 52, 626–628, 1998.
14. J. F. Aust, J. B. Cooper, K. L. Wise, and B. J. Jensen, "In Situ Analysis of a High-Temperature Cure Reaction in Real Time Using Modulated Fiber-Optic FT-Raman Spectroscopy", *Applied Spectroscopy*, 53, 682–686, 1999.
15. B. J. Marquardt, S. M. Angel, J. C. Carter, D. N. Stratis, and W. E. Brewer, "Some new uses for filtered fiber-optic Raman probes: In situ drug identification and in situ and remote Raman imaging", *Journal of Raman Spectroscopy*, 30, 795–805, 1999.
16. X. Zheng, W. Fu. S. Albin, K. L. Wise, A. Javey, and J. B. Cooper, "Self-Referencing Raman Probes for Quantitative Analysis", *Applied Spectroscopy*, 55, 382–388, 2001.
17. T. F. Cooney, H. T. Skinner, and S. M. Angel, "Comparative Study of Some Fiber-Optic Remote Raman Probe Designs. Part I: Model for liquids and Transparent Solids", *Applied Spectroscopy*, 50, 836–848, 1996.
18. T. F. Cooney, H. T. Skinner, and S. M. Angel, "Comparative Study of Some Fiber-Optic Remote Raman Probe Designs. Part II: Tests of Single-Fiber, Lensed, and Flat- and Bevel-Tip Multi-Fiber Probes", *Applied Spectroscopy*, 50, 849–860, 1996.

We claim:

1. A spectroscopic analysis method for detecting the presence or measuring the concentration of analytes in a sample, said method comprising the steps of:
   providing a collimated incident optical beam;
   directing said collimated incident optical beam through an optical immersion probe comprising a probe housing tube having a first end at an opening and a second end, a spherical lens fixed within said opening of said probe housing tube, and a seal positioned between said spherical lens and said probe housing tube, wherein said spherical lens focuses said incident optical beam;
   contacting said optical immersion probe with said sample wherein said spherical lens is in physical contact and optical contact with said sample, and wherein said spherical lens provides an optical and sample interface, illuminating said sample with said incident optical beam;
   collecting scattered light from said analytes with said spherical lens, thereby generating a beam of scattered light; and
   analyzing and detecting said beam of scattered light with a photodetector, thereby detecting the presence of analytes in the sample, measuring the concentration of analytes in the sample or both.

2. The spectroscopic analysis method of claim 1 wherein said analyzing step comprises passing said scattered light through a Raman spectrometer.

3. The spectroscopic analysis method of claim 1 wherein said spectroscopic analysis method provides a Raman spectroscopy measurement.

4. The spectroscopic analysis method of claim 1 wherein said spectroscopic analysis method provides a Fourier Transform infrared spectroscopy measurement.

5. The spectroscopic analysis method of claim 1 wherein said spectroscopic analysis method provides an infrared spectroscopy measurement.

6. The spectroscopic analysis method of claim 1 wherein said spectroscopic analysis method provides a visible light spectroscopy measurement.

7. The spectroscopic analysis method of claim 1 wherein said spectroscopic analysis method provides an ultra-violet light spectroscopy measurement.

8. The spectroscopic analysis method of claim 1 wherein said incident optical beam comprises light having wavelengths in the visible region of the electromagnetic spectrum.

9. The spectroscopic analysis method of claim 1 wherein said incident optical beam comprises light having wavelengths in the ultraviolet region of the electromagnetic spectrum.

10. The spectroscopic analysis method of claim 1 wherein said incident optical beam comprises light having wavelengths in the infrared region of the electromagnetic spectrum.

11. The spectroscopic analysis method of claim 10 wherein said incident optical beam comprises light having wavelengths in the mid-infrared region of the electromagnetic spectrum.

12. The spectroscopic analysis method of claim 10 wherein said incident optical beam comprises light having wavelengths in the near-infrared region of the electromagnetic spectrum.

13. The spectroscopic analysis method of claim 1 wherein said spherical lens is a ball lens.

14. The spectroscopic analysis method of claim 1 wherein said spherical lens has a shape approximating the form of at least a portion of a geometric sphere.

15. The spectroscopic analysis method of claim 1 wherein said spherical lens provides a constant focal length.

16. The spectroscopic analysis method of claim 1 wherein the distance between the apex of said spherical lens and the focal point of said spherical lens is between about 50 microns to about 200 microns.

17. The spectroscopic analysis method of claim 1 wherein said spherical lens provides a constant focal volume.

18. The spectroscopic analysis method of claim 1 wherein said seal is selected from the group consisting of:
   a weld;
   a braise;
   an adhesive layer; and
   a gasket.

19. The spectroscopic analysis method of claim 1 wherein said seal is an o-ring seal.

20. The spectroscopic analysis method of claim 1 wherein said seal is a substantially leak proof seal.

21. The spectroscopic analysis method of claim 20 wherein said substantially leak proof seal is leak proof for pressures up to about 1000 psi Helium.

22. The spectroscopic analysis method of claim 1 wherein said sample is selected from the group consisting of:
   a solid;
   a liquid;
   a powder;
   a suspension;
   particles;
   a slurry; and
   a vapor.

23. A spectroscopic analysis method for detecting the presence or measuring the concentration of analytes in a sample, said method comprising the steps of:
   providing a collimated incident optical beam;
   directing said collimated incident optical beam through an optical immersion probe comprising a probe housing tube having a first end at an opening and a second end, a spherical lens fixed within said opening of said probe housing tube, and a seal positioned between said spherical lens and said probe housing tube, wherein said spherical lens focuses said incident optical beam;
   contacting said optical immersion probe with said sample wherein said spherical lens is in physical contact and optical contact with said sample, and wherein said spherical lens provides an optical and sample interface,
   illuminating said sample with said incident optical beam;
   collecting fluorescent light from said analytes in said sample with said spherical lens, thereby generating a beam of fluorescent light; and
   analyzing and detecting said beam of fluorescent light with a photodetector, thereby detecting the presence of analytes in the sample, measuring the concentration of analytes in the sample or both.

24. The spectroscopic analysis method of claim 23 wherein said incident optical beam comprises light having wavelengths in the visible region of the electromagnetic spectrum.

25. The spectroscopic analysis method of claim 23 wherein said incident optical beam comprises light having wavelengths in the ultraviolet region of the electromagnetic spectrum.

* * * * *